United States Patent [19]

Mathur

[11] Patent Number: 5,405,615

[45] Date of Patent: Apr. 11, 1995

[54] SUCROSE DISTEARATE LIPID VESICLES

[75] Inventor: Rajiv Mathur, Sewell, N.J.

[73] Assignee: Micro Vesicular Systems, Inc., Nashua, N.H.

[21] Appl. No.: 148,885

[22] Filed: Nov. 8, 1993

Related U.S. Application Data

[63] Continuation-in-part of Ser. No. 761,253, Sep. 17, 1991, Pat. No. 5,260,065.

[51] Int. Cl.$^6$ .............................................. A61K 9/127
[52] U.S. Cl. ................................. 424/450; 428/402.2
[58] Field of Search ................. 424/450; 428/402.2; 436/829

[56] References Cited

U.S. PATENT DOCUMENTS

| | | | |
|---|---|---|---|
| 3,069,370 | 12/1962 | Jensen et al. | 260/23 |
| 3,372,201 | 5/1968 | Leary et al. | 260/615 |
| 3,957,971 | 5/1976 | Oleniacz | 424/70 |
| 4,075,131 | 2/1978 | Sterling | 252/542 |
| 4,182,330 | 10/1980 | Michaels | 128/260 |
| 4,235,871 | 11/1980 | Papahadjopoulos | 424/19 |
| 4,241,046 | 12/1980 | Papahadjopoulos | 424/19 |
| 4,247,411 | 1/1981 | Vanlerberghe et al. | 252/316 |
| 4,271,344 | 8/1980 | Vanlerberghe et al. | 424/60 |
| 4,348,329 | 9/1982 | Chapman | 268/483 |
| 4,356,167 | 10/1982 | Kelly | 424/38 |
| 4,377,567 | 3/1983 | Geho | 424/1 |
| 4,399,313 | 8/1983 | Vanlerberghe et al. | 568/622 |
| 4,465,860 | 8/1984 | Vanlerberghe et al. | 568/36 |
| 4,536,324 | 8/1985 | Fujiwara | 252/311 |
| 4,544,545 | 10/1985 | Ryan et al. | 424/1.1 |
| 4,551,288 | 11/1985 | Kelly | 264/4.6 |
| 4,610,868 | 9/1986 | Fountain et al. | 424/1.1 |
| 4,666,711 | 5/1987 | Vanlerberghe et al. | 424/70 |
| 4,695,554 | 9/1987 | O'Connell et al. | 436/528 |
| 4,725,442 | 2/1988 | Haynes | 424/490 |
| 4,731,210 | 3/1988 | Weder et al. | 264/4.3 |
| 4,744,989 | 5/1988 | Payne | 424/490 |
| 4,762,915 | 8/1988 | Kung et al. | 530/405 |
| 4,772,471 | 9/1988 | Vanlerberghe et al. | 424/450 |
| 4,789,633 | 12/1988 | Huang et al. | 435/240 |
| 4,832,872 | 5/1989 | Scandel | 252/547 |
| 4,855,090 | 8/1989 | Wallach | 264/4.1 |
| 4,897,308 | 1/1990 | Vanlerberghe et al. | 428/402 |
| 4,911,928 | 3/1990 | Wallach | 424/450 |
| 4,917,951 | 4/1990 | Wallach | 428/402 |
| 5,019,392 | 5/1991 | Wallach | 424/420 |
| 5,021,200 | 6/1991 | Vanlerberghe et al. | 264/4.3 |
| 5,032,457 | 7/1991 | Wallach | 428/402 |
| 5,160,669 | 11/1992 | Wallach | 264/43 |

FOREIGN PATENT DOCUMENTS

| | | |
|---|---|---|
| 0032578 | 12/1980 | European Pat. Off. |
| 0167825 | 6/1985 | European Pat. Off. |
| 59-106423 | 6/1984 | Japan |
| 61-207324 | 9/1986 | Japan |
| 1539625 | 1/1979 | United Kingdom |
| 2078543 | 1/1982 | United Kingdom |
| 2079179 | 1/1982 | United Kingdom |
| 2147263 | 5/1985 | United Kingdom |
| 2166107 | 4/1986 | United Kingdom |
| 8706499 | 5/1987 | WIPO |

OTHER PUBLICATIONS

Gregoriadis, G., Liposome Technology 2nd Ed. vol. 7, Chp. 9 (1993) 141–155.
Schenk et al., J. Micro. Encaps. 6:95–103 (1989).
Ishigami et al., JAOCS 66(4):599 (1989).
McCuthcheon, "Detergents and Emulsifiers", No. American Edition (1973).
Handjani-Villa, "Les Niosomes" (1985).
Baille et al., J. Pharm. Pharmacol 38:502–505 (1986).
Dousset et al., "Methods de Preparation des Liposomes ..." (1985).
Ribier et al., Colloids and Surfaces 10:155–161 (1984).
Szoha et al., Proc. Nat'l. Acad Sci. USA 75:4194–4198 (1978).
Baillie et al., J. Pharm. Pharmacol. 37:863–868 (1985).
Puisieux et al., "Problemes Technologiques Poses Par L'utilisation des Liposomes ..." (1985).
Murahami et al., J. Org. Chem. 47:2137–2144 (1982).
Gregoriadis, N. E. J. Med. 13:704–710 (1976).
Bangham et al. J. Mol. Biol. 13:238–252 (1965).

Primary Examiner—Gollamudi S. Kishore

[57] ABSTRACT

Disclosed are lipid vesicles containing a blend of amphiphiles, including sucrose distearate, in the lipid bilayers. The vesicles may have either an aqueous or oil-filled central cavity and are particularly useful for delivering dermatological, cosmetic and pharmaceutical formulations. A method of manufacture for these vesicles is also disclosed.

8 Claims, No Drawings

SUCROSE DISTEARATE LIPID VESICLES

REFERENCE TO RELATED APPLICATION

This application is a continuation-in-part of the U.S. patent application Ser. No. 07/761,253, filed on Sep. 17, 1991, (Attorney Docket No. IMH-121), now U.S Pat. No. 5,260,065.

BACKGROUND OF THE INVENTION

The present invention relates to formulations for lipid vesicles and methods of their manufacture. More particularly, the present invention discloses paucimellar lipid vesicles designed of materials which have exceptional properties for cosmetic, edible, dermatological, and pharmaceutical use. The paucimellar vesicles of the invention have 2–10 lipid bilayers surrounding a large amorphous central cavity which can contain a water-immiscible oily material or an aqueous solution. These lipid vesicles have a combination of sucrose distearate and at least one other compatible amphiphile as the primary structural material of their lipid bilayers.

Lipid vesicles are substantially spherical structures made of amphiphiles, e.g., surfactants or phospholipids. The lipids of these spherical vesicles are generally organized in the form of lipid bilayers, e.g., multiple onion-like shells of lipid bilayers which encompass an aqueous volume between the bilayers. Paucilamellar lipid vesicles have 2–10 peripheral bilayers which surround a large, unstructured central cavity.

Until recently, liposome technology has been concerned mostly with vesicles composed of phospholipids. This is primarily because phospholipids are the principal structural components of natural membranes and, accordingly, lipid vesicles have been used as a model system for studying natural membranes. However, there are a number of problems associated with using phospholipids as synthetic membranes. Biological membranes are stabilized by membrane proteins and maintained by extensive enzymatic "support" systems that rapidly turn over, exchange or modify membrane lipids. Neither membrane proteins nor the requisite enzymatic support systems can be practically incorporated into the wall structure of liposomes, making the structures inherently less stable than natural membranes. In addition, the biological environment contains several potent phospholipases that rapidly break down free phospholipids. These phospholipases will attack liposomes and degrade the membrane. For these reasons, phospholipid liposomes placed in an in vivo environment are rapidly degraded.

Moreover, phospholipid liposome technology has other problems. Phospholipids are labile and expensive to purify or synthesize. In addition, classic phospholipid liposomes are in the form of multilamellar as opposed to paucilamellar vesicles and have poor carrying capacities, especially for lipophilic materials, and have poor shelf lives unless lyophilized in the dark with antioxidants. Finally, phospholipids degrade too rapidly in vivo for most pharmaceutical or vaccine applications.

For these reasons, there is increasing interest in liposomes made of commercially available nonphospholipid amphiphiles (see, e.g. U.S. Pat. No. 4,217,344, U.S Pat. No. 4,917,951, and U.S. Pat. No. 4,911,928). These molecules have a hydrophilic head group attached to a hydrophobic "tail" and are derived from long chain fatty acids, long chain alcohol's and their derivatives, long chain amines, and polyol sphingo- and glycerolipids. Commercially available amphiphile surfactants include the BRIJ family of polyoxyehtylene fatty ethers, the SPAN sorbitan fatty acid esters, and the TWEEN polyoxyehtylene derivatives of sorbitan fatty acid esters, all available from ICI Americas, Inc. of Wilmington, Del. Paucilamellar vesicles comprised of such amphiphiles provide a high carrying capacity for water-soluble and water immiscible substances. The high capacity for water immiscible substances represents a unique advantage over classical phospholipid multilamellar liposomes.

Use of lipid vesicles in the fields of cosmetics, edibles, dermatologicals and pharmaceuticals is rapidly expanding. Many cosmetic and dermatological preparations commonly include amphiphiles such as propylene glycol stearate, stearyl alcohol, polyoxyethylene fatty ethers (i.e., POE 10 stearyl alcohol), sorbitan fatty acid esters, and polyoxyethylene derivatives of sorbitan fatty acid esters (i.e., POE 20 sorbitan monostearate). These additives can be used as emulsifiers or thickeners, providing the "feel" to certain cosmetics and/or dermatologicals. These additives also fall under the GRAS list and can therefore be used in many food and pharmaceutical products. It would therefore be advantageous to use these amphiphiles as the lipid vesicle formers.

Accordingly, an object of the present invention is to provide a method of making paucimellar lipid vesicles using as primary structural lipids of the bilayers amphiphiles which are commonly used in cosmetics, dermatologicals and pharmaceuticals.

Another object of the invention is to provide paucilamellar lipid vesicles which contain sucrose distearate and at least one other amphiphile as the structural lipids of the bilayers.

A further object of the invention is to provide a method of producing paucimellar lipid vesicles which readily encapsulate water immiscible oily materials and are manufactured from relatively inexpensive materials.

These and other objects and features of the invention will be apparent from the following description and the claims.

SUMMARY OF THE INVENTION

The present invention features lipid vesicles and a method of manufacture using a blend of sucrose distearate and at least one other amphiphile as the major lipid components of the bilayers. These blended vesicles feature materials with special usefulness for cosmetic, dermatological, and pharmaceutical processes and products.

The vesicles of the invention have about two-ten bilayers arranged in the form of substantially spherical shells separated by aqueous layers surrounding a large amorphous central cavity free of lipid bilayers. The lipid bilayers have as their primary lipid components a mixture of sucrose distearate and at least one other amphiphile selected from the group consisting of fatty alcohols, quaternary dimethyldiacyl amines, polyoxyethylene acyl alcohols, polyglycerols, sorbitan fatty acid esters, ethoxylated sorbitan fatty acid esters, fatty acids and their salts, and mixtures thereof. In particular, propylene glycol stearate is mixed with stearyl alcohol, polyoxyethylene fatty alcohols, polyoxyethylene derivatives of sorbitan fatty acid esters having 10–20 oxyethylene groups, and mixtures thereof; wherein the fatty alcohol or fatty acid groups of the polyoxyethylene fatty alcohols and the polyoxyethylene derivatives of sorbitan fatty acid esters are selected from the group consisting of radicals of palmetic acid, stearic acid, lauric acid, and oleic acid, and mixtures thereof. This mixture may further contain at least one sterol selected from the group consisting of cholesterol, cholesterol derivatives, hydrocortisone, phytosterol, and mixtures thereof, a charge producing agent, and any lipid soluble materials to be incorporated into the vesicles.

The vesicles of the invention have an amorphous central cavity carrying either water soluble materials or a water-immiscible oily solution. The basic requirement for this water-immiscible oily solution is that it is made of materials which are both water immiscible and immiscible in the lipids used to form the bilayers. Examples of these water-immiscible oily materials include mineral oils, soybean oil, paraffin waxes, petrolatum, triglyceride oils and fats, perfumes and fragrances, flavor oils, perfluorocarbon liquids, water insoluble vitamins, and a variety of water-immiscible solvents. Of particular interest is the encapsulation of anthralin or retinoic acid as the water-immiscible material. These materials provide pharmacological or dermatological benefits in addition to the benefits caused by the use of the particular lipids which form the bilayers.

The invention further features a method of producing the lipid vesicles of the invention. Oil filled vesicles, e.g., vesicles having their amorphous central cavities filled with a water-immiscible oily solution, may be formed using either the "hot loading" technique disclosed in U.S. Pat. No. 4,911,928 or the "cold loading" technique described in the U.S. Pat. No. 5,160,669, the disclosures of which are incorporated herein by reference. In either case, a lipid phase is formed by blending propylene glycol stearate and the compatible amphiphile(s), along with any sterols or lipophilic materials to be incorporated into the lipid bilayers, to form a homogenous lipid phase. In the "hot loading" technique, any water-immiscible oily material to be encapsulated in the vesicles is blended in the already formed lipid phase, forming a lipophilic phase. If any oil-soluble or oil-suspendable materials are to be encapsulated within the vesicles, they are first dispersed in the oil. The term "dispersed" as used herein includes dissolution or forming a suspension or colloid to yield a flowable phase.

Once a lipophilic phase is made, it is blended with an aqueous phase (e.g., water, saline, or any other aqueous solution which will be used to hydrate the lipids) under shear mixing conditions to form the vesicles. "Shear mixing conditions", as used herein, means a shear equivalent to a relative flow of 5–50 m/s through a 1 mm orifice.

In the "cold loading" technique, the lipid phase and the aqueous phase are blended under shear mixing conditions to form vesicles. These vesicles are then blended under low shear conditions, as described in the aforementioned U.S. Pat. No. 5,160,669.

All of the materials used to form the vesicles of the invention can also be used in the methods of the invention. Other modifications of the methods and products will be apparent from the following description and the claims.

DETAILED DESCRIPTION OF THE INVENTION

The present invention uses a blend of amphiphiles to form paucilamellar lipid vesicles. In particular, sucrose distearate is blended with at least one other amphiphile to form a lipid phase which can be hydrated to form vesicles. Other additives, such as a sterol, may also be blended with the lipid phase.

The preferred other amphiphiles to be used in the lipid phase are stearyl alcohol, polyoxyethylene fatty alcohols, polyoxyethylene derivatives of sorbitan fatty acid esters having 10–20 oxyethylene groups, and mixtures thereof; wherein the fatty alcohol or fatty acid groups of the polyoxyethylene fatty alcohols and the polyoxyethylene derivatives of sorbitan fatty acid esters are selected from the group consisting of radicals of palmetic acid, stearic acid, lauric acid, and oleic acid, and mixtures thereof. In a preferred embodiment of the invention, the lipid mixture of the invention contains propylene glycol stearate, stearyl alcohol and polyoxyethylene 20 sorbitan monostearate (Polysorbate 60). This mixture may further contain at least one sterol selected from the group consisting of cholesterol, cholesterol derivatives, hydrocortisone, phytosterol, and mixtures thereof, and any other materials to be incorporated into the bilayers.

The lipid vesicles of the invention are paucilamellar lipid vesicles characterized by two to ten lipid bilayers or shells with small aqueous volumes separating each substantially spherical lipid shell. The innermost lipid bilayer surrounds a large, substantially amorphous central cavity which may be filled with either an aqueous solution or a water-immiscible oily solution.

Examples of water-immiscible oily materials which can be encapsulated in the central cavity are mineral oils, soybean oil, paraffin waxes, petrolatum, triglyceride oils and fats, perfumes and fragrances, flavor oils, perfluorocarbon liquids, anthralin, retinoic acid, water insoluble vitamins, and water immiscible solvents. Avocado oil unsaponifiables can also be encapsulated in the central cavity and is particularly useful as it may additionally be used as a source of phytosterol to stabilize the vesicle bilayer.

The following Examples will clearly illustrate the efficacy of the invention.

EXAMPLE 1

In this Example, both aqueous-filled and oil-filled lipid vesicles were formed using a blend of sucrose distearate and other amphiphiles and/or sterols. Other amphiphiles included stearyl alcohol, polyoxyethylene 20 sorbitan monostearate (Polysorbate 60), and polyoxyethylene 10 stearyl alcohol (Brij 76). Other sterols included cholesterol, soybean oil and avocado oil unsaponifiables.

TABLE 1

| Composition (grams) | Sample | | | | | |
|---|---|---|---|---|---|---|
|  | A | B | C | D | E | F |
| Sucrose distearate | 4.25 | 2.55 | 2.5 | 2.5 | 2.0 | 2.0 |
| Stearyl Alcohol |  |  | 0.5 | 0.5 |  |  |
| Polysorbate 60 |  | 0.67 |  |  |  |  |
| Brij 76 |  |  |  |  | 1.6 | 1.2 |
| Avocado oil Unsaponifiables |  | 4.0 |  |  | 4.0 | 5.0 |
| Cholesterol | 0.75 |  | 1.25 | 1.25 |  |  |
| Soybean Oil |  |  |  | 1.75 |  |  |
| Water | 30 | 35 | 30 | 30 | 40 | 40 |

| Composition (grams) | Sample | | | | |
|---|---|---|---|---|---|
|  | G | H | I | J | K |
| Sucrose Distearate | 2.0 | 2.5 | 2.5 | 2.0 | 2.5 |
| Stearyl Alcohol | 0.5 | 0.5 | 0.75 | 0.5 | 0.35 |
| Polysorbate 60 |  | 0.35 | 0.5 | 0.7 | 0.35 |
| Brij 76 | 1.1 |  |  |  |  |
| Avocado Oil Unsaponifiables | 4.0 |  |  | 4.0 | 4.0 |

TABLE 1-continued

| | | | | |
|---|---|---|---|---|
| Cholesterol | | 1.25 | 1.25 | 0.3 | 0.3 |
| Soybean Oil | | 1.75 | | | |
| Water | 40 | 30 | 30 | 35 | 35 |

For samples A, C and I, aqueous-filled lipid vesicles were formed by first blending the sucrose distearate and the applicable amphiphiles and/or cholesterol at approximately 80° C. with water at 70° C. Hydration to form lipid vesicles was then achieved by shear mixing the lipid and aqueous phases using two 60 cc syringes, connected by a stopcock. The lipid and aqueous phases were blended from one syringe to the other, forming aqueous-filled vesicles in two minutes or less. However, in this and the following Examples, any method of achieving the proper shear could be used. Preferably, a flow device such as the Novamix ™ vesicle former is used. The basic details of the Novamix ™ system are described in U.S. Pat. No. 4,895,452, the disclosure of which is incorporated herein by reference.

For samples B, D–H, and J–K oil-filled vesicles were formed using the hot loading technique described in U.S. Pat. No. 4,911,928, the disclosure of which is incorporated herein by reference. Briefly, in order to hot load the vesicles, the soybean oil or avocado oil unsaponifiables was heated to 82° C., blended with the lipid phase, and then the combined lipid/oily phase was hydrated by the aqueous phase at 70° C. using the syringe method described above. Either hot loading or cold loading techniques may be used for soybean oil and avocado oil unsaponifiables.

Sample A was designed to form lipid vesicles using sucrose distearate as the only amphiphile in the lipid bilayers. After processing to form lipid vesicles, the sample had a fluid consistency and microscopic examination showed poor, hetro-sized vesicles. This result indicated the need to add another amphiphile or spacer molecule in the mixture making up the lipid walls, probably due to the large size of the sucrose distearate molecules. No separation was observed after centrifugation at 3500 rpm for 15 minutes.

Samples B–F were designed to form both oil-filled and aqueous-filled lipid vesicles using only one amphiphile or spacer in addition to sucrose distearate, as the materials forming the lipid bilayers. The spacers used were stearyl alcohol, Polysorbate 60 or Brij 76. After processing to form lipid vesicles, all of these samples had a fluid consistency and an off-white color, probably due to the cream color of the sucrose distearate.

Upon microscopic examination of samples B–F, the following observations were made:

Sample B showed many hetro-sized vesicles with rough surfaces and irregular cores. All vesicles were birfringent with maltese cross patterns visible, indicating multiple concentric lipid bilayers.

Samples C and D showed very poor, irregular-shaped, birfringent vesicles.

Sample E showed the best vesicle formation. The vesicles were quite homogenous and mostly hetro-sized. Birfringence with maltese crosses was also observed, indicating multiple concentric lipid bilayers.

Sample F showed hetro-sized vesicles, much like those in sample E, but the vesicles had rough surfaces.

After centrifugation of samples B–F, sample E showed approximately 5 ml of turbid, aqueous phase separation at the bottom of the samples, probably due to an excess of water in this sample. Sample F showed approximately 2–3 ml of separation, probably due to an excess of water in this sample. Samples B–D all showed no separation.

Overall, samples B–F show that lipid vesicles formed with sucrose distearate and only one other amphiphile consisting of stearyl alcohol or Polysorbate 60 tend to be poorly shaped and irregular. However, when Brij 76 is used as the only other amphiphile making up the lipid bilayers, along with sucrose distearate, then good lipid vesicle formation is achieved.

Samples G–K were designed to form both aqueous-filled and oil-filled lipid vesicles using a combination of two amphiphiles in addition to sucrose distearate as the principal materials making up the lipid bilayers. Sample G contained stearyl alcohol and Brij 76 as the spacers, whereas samples H–K all contained stearyl alcohol and Polysorbate 60.

After processing to form lipid vesicles, all samples G–K had a fluid consistency, except for sample H which was more lotion-like (probably due to the lesser amount of Polysorbate 60 and water). Upon microscopic examination, the following results were observed:

Sample G showed mostly nice, hetro-sized vesicles mixed with a few tear drop shaped vesicles with irregular cores.

Sample H showed many small nicely-formed vesicles mixed with a few very large, birefringent vesicles.

Sample I showed the same vesicles as H, except that the vesicles were aggregated.

Sample J showed mostly hetro-sized vesicles, some with irregular cores.

Sample K showed mostly hetro-sized vesicles, some with rough surfaces.

After centrifugation of samples G–K, sample H showed approximately 5 ml of turbid, aqueous phase separation at the bottom of the sample, probably due to an excess of water in this sample. Samples G and K showed approximately 2–3 ml of separation, probably due to an excess of water in these samples. All other samples showed no separation.

Overall, samples G–K show that lipid vesicles formed by using two amphiphiles or spacers in addition to sucrose distearate as the principal materials in the lipid bilayers tend to be nicely shaped hetro-sized vesicles. By hot loading these vesicles with an oil, preferably soybean oil (as in sample H) or avocado oil unsaponifiables, which provides the additional benefit of acting as a structural component in the lipid bilayers (as in samples J and K), further homogeneity in the lipid vesicle population can be achieved.

The foregoing Examples are merely illustrative and those skilled in the art may be able to determine other materials and methods which accomplish the same results. Such other materials and methods are included within the following claims.

What is claimed is:

1. A paucilamellar lipid vesicle having 2–10 bilayers surrounding an amorphous central cavity, the amphiphiles of each of said bilayers consisting essentially of a mixture of sucrose distearate and at least one other amphiphile selected from the group consisting of stearyl alcohol, polyoxyethylene fatty alcohols, polyoxyethylene derivatives of sorbitan fatty acid esters having 10–20 oxyethylene groups, and mixtures thereof; and wherein the fatty alcohol or fatty acid groups of the polyoxyethylene fatty alcohols and the polyoxyethylene derivatives of sorbitan fatty acid esters are selected from the group consisting of fatty alcohols and esters of palmetic acid, stearic acid, lauric acid, and oleic acid, and mixtures thereof.

2. The lipid vesicle of claim 1 wherein said other amphiphile comprises polyoxyethylene 20 sorbitan monostearate.

3. The lipid vesicle of claim 2 wherein said other amphiphile comprises stearyl alcohol.

4. The lipid vesicle of claim 1 wherein said other amphiphile is polyoxyethylene 10 stearyl alcohol.

5. The lipid vesicle of claim 1 wherein said bilayers further comprises at least one sterol selected from the group consisting of cholesterol, hydrocortisone, phytosterol, and mixtures thereof.

6. The lipid vesicle of claim 4 wherein said paucilamellar lipid vesicle comprises an amorphous central cavity containing a water immiscible material.

7. The lipid vesicle of claim 6 wherein said water immiscible material is selected from the group consisting of mineral oils, soybean oil, paraffin waxes, petrolatum, triglyceride oils and fats, perfumes and fragrances, flavor oils, perfluorocarbon liquids, anthralin, retinoic acid, water insoluble vitamins, water immiscible solvents and mixtures thereof.

8. The paucilamellar lipid vesicles of claim 5 wherein said phytosterol is provided from avocado oil unsaponifiables.

* * * * *